US011413231B2

(12) United States Patent
Garcés Gómez de Aranda et al.

(10) Patent No.: US 11,413,231 B2
(45) Date of Patent: Aug. 16, 2022

(54) COSMETIC HAIR DYEING AND/OR BLEACHING COMPOSITION, METHOD, USE AND KIT THEREOF

(71) Applicant: Revlon Consumer Products Corporation, New York, NY (US)

(72) Inventors: Carlos Garcés Gómez de Aranda, Barcelona (ES); María Victoria Lovelle Iglesias, Sant Joan Despí (ES); Rocio Vallecillos López, Barcelona (ES)

(73) Assignee: Revlon Consumer Products Corporation, New York, NY (US)

( * ) Notice: Subject to any disclaimer, the term of this patent is extended or adjusted under 35 U.S.C. 154(b) by 30 days.

(21) Appl. No.: 17/049,717

(22) PCT Filed: Apr. 23, 2019

(86) PCT No.: PCT/EP2019/060395
§ 371 (c)(1),
(2) Date: Oct. 22, 2020

(87) PCT Pub. No.: WO2019/206920
PCT Pub. Date: Oct. 31, 2019

(65) Prior Publication Data
US 2021/0244639 A1    Aug. 12, 2021

(30) Foreign Application Priority Data
Apr. 24, 2018 (EP) .................................... 18382279

(51) Int. Cl.
*A61Q 5/10* (2006.01)
*A61K 8/44* (2006.01)
*A61K 8/55* (2006.01)
*A61Q 5/08* (2006.01)
*A61Q 5/12* (2006.01)

(52) U.S. Cl.
CPC ............... *A61K 8/44* (2013.01); *A61K 8/55* (2013.01); *A61Q 5/08* (2013.01); *A61Q 5/10* (2013.01); *A61Q 5/12* (2013.01); *A61K 2800/4324* (2013.01); *A61K 2800/805* (2013.01); *A61K 2800/882* (2013.01)

(58) Field of Classification Search
CPC . A61Q 5/10; A61Q 5/065; A61Q 5/08; A61K 8/22; A61K 2800/4324; A61K 2800/882; A61K 2800/88; A61K 8/55; A61K 2800/51; A61K 8/24
USPC .......................................................... 8/405
See application file for complete search history.

(56) References Cited

U.S. PATENT DOCUMENTS

| | | | |
|---|---|---|---|
| 8,343,238 B1* | 1/2013 | Lopez | A61K 8/44 8/405 |
| 2004/0055095 A1* | 3/2004 | McKelvey | A61K 8/55 8/405 |
| 2004/0086475 A1* | 5/2004 | Boswell | A61Q 5/08 424/70.2 |
| 2004/0105830 A1* | 6/2004 | Boswell | A61Q 5/04 424/70.2 |
| 2004/0123402 A1* | 7/2004 | Marsh | A61Q 5/08 8/405 |
| 2004/0237218 A1* | 12/2004 | Marsh | A61K 8/60 8/405 |
| 2006/0117493 A1* | 6/2006 | Bureiko | A61K 8/731 8/405 |
| 2006/0117498 A1* | 6/2006 | Bureiko | A61K 8/556 8/406 |
| 2008/0010754 A1* | 1/2008 | Bureiko | A61K 8/19 8/406 |
| 2011/0318293 A1* | 12/2011 | Kleen | A61Q 5/04 424/70.2 |
| 2013/0167861 A1* | 7/2013 | Lopez | A61Q 5/04 132/204 |
| 2013/0167862 A1* | 7/2013 | Lopez | A61K 8/42 132/208 |
| 2015/0166253 A1* | 6/2015 | Nomura | B65B 3/00 222/402.1 |
| 2016/0158130 A1* | 6/2016 | Mori | A61Q 5/10 8/435 |

FOREIGN PATENT DOCUMENTS

| | | |
|---|---|---|
| FR | 2944963 A1 | 11/2010 |
| JP | 2004161707 A | 6/2004 |
| JP | 2009107998 A | 5/2009 |
| WO | 02089754 A1 | 11/2002 |
| WO | 2008153050 A1 | 12/2008 |
| WO | 2013131576 A1 | 9/2013 |
| WO | 2019206920 A1 | 10/2019 |

OTHER PUBLICATIONS

International Search Report and Written Opinion received for International Application No. PCT/EP2019/060395, dated Jul. 19, 2019, 10 pages.

* cited by examiner

*Primary Examiner* — Eisa B Elhilo
(74) *Attorney, Agent, or Firm* — Dorsey & Whitney LLP

(57) ABSTRACT

The present disclosure relates to a composition containing at least one chelating agent, its use, a hair dyeing and/or bleaching composition which contains this composition, a kit for dyeing and/or bleaching hair which comprises the composition, a method for dyeing and/or bleaching the hair, and a method for hair cosmetic treatment which comprise the application of the composition.

12 Claims, No Drawings

COSMETIC HAIR DYEING AND/OR BLEACHING COMPOSITION, METHOD, USE AND KIT THEREOF

CROSS REFERENCE TO RELATED APPLICATIONS

This application claims priority under 37 CFR 3.71 to International Patent Application No. PCT/EP2019/060395, filed Apr. 23, 2019, entitled "A COSMETIC HAIR DYEING AND/OR BLEACHING COMPOSITION, METHOD, USE AND KIT THEREOF," which in turn claims priority to European Patent Application No. 18382279.0, filed Apr. 24, 2018, entitled "A COSMETIC HAIR DYEING AND/OR BLEACHING COMPOSITION, METHOD, USE AND KIT THEREOF", each of which is incorporated by reference herein, in the entirety and for all purposes.

TECHNICAL FIELD

The present disclosure relates to a composition, its use, a hair dyeing and/or bleaching composition, a kit for dyeing and/or bleaching hair, a method for dyeing and/or bleaching the hair, and a method for hair cosmetic treatment.

BACKGROUND

Hair dyeing or bleaching have been common treatments of the human hair in the cosmetic industry for almost one century. The most popular hair dyeing treatment is the permanent oxidative dyeing, which, in summary, comprises the application in the hair of a ready-to-use mixture of a dyeing composition containing oxidation dye precursors and an oxidizing composition comprising an oxidant, normally hydrogen peroxide. Bleaching treatments comprise the application in the hair of a ready-to-use mixture of a composition comprising bleaching agents and oxidizing compositions containing hydrogen peroxide.

Human hair contains pollutant cationic metals, like transition metals, absorbed from tap water or air. These cationic metals catalyze the formation of free radical species such as hydroxyl radical (OH*) by reaction with hydrogen peroxide. It is well known that free radical species provoke damage in the keratin fibers, i.e., in hair. Moreover, not all hydrogen peroxide reacts with the oxidation dye precursors, but with the cationic metals, leading to a color deviation from the expected color of the dye and chromaticity deviation of the ready-to-use hair dyeing and/or bleaching composition applied to the hair.

There is the need in the state of the art of new compositions which disable the pollutant cationic metals in the hair before they react with the hydrogen peroxide of the ready-to-use dyeing and/or bleaching composition, and therefore. A composition that achieves these goals will prevent or minimize hair damage by free radicals, color deviation in the hair, or chromaticity deviation.

SUMMARY

In a first aspect, the composition is a composition having an alkaline pH and comprising an effective amount of at least one chelating agent, suitable for chelating cationic transition metals in an oxidation alkali medium.

In another aspect, the composition comprises a cosmetically effective amount of at least one chelating agent, suitable for chelating cationic transition metals in an oxidation alkali medium; at least one hair oxidative dyeing or bleaching agent; and wherein the composition is a hair dyeing and/or bleaching composition having an alkaline pH.

In a third aspect, the composition comprises a cosmetically effective amount of at least one chelating agent dissolved in a water-based medium, suitable for chelating cationic transition metals in an oxidation alkali medium; at least one hair oxidative dyeing or bleaching agent; at least one oxidant, and wherein the composition is a ready-to-use hair dyeing and/or bleaching composition having an alkaline pH.

In a fourth aspect, the kit for dyeing and/or bleaching hair comprises individually packaged a) a composition having an alkaline pH and comprising an effective amount of at least one chelating agent, suitable for chelating cationic transition metals in an oxidation alkali medium; b) a hair dyeing and/or bleaching composition comprising at least one hair oxidative dyeing or bleaching agent, and c) an oxidizing composition comprising at least one oxidant.

In a fifth aspect, the kit for dyeing and/or bleaching hair comprises individually packaged a) a composition comprising a cosmetically effective amount of at least one chelating agent, suitable for chelating cationic transition metals in an oxidation alkali medium; at least one hair oxidative dyeing or bleaching agent; wherein the composition is a hair dyeing and/or bleaching composition having an alkaline pH; and b) an oxidizing composition comprising at least one oxidant.

In a sixth aspect, the use of a composition having an alkaline pH and comprising an effective amount of at least one chelating agent, suitable for chelating cationic transition metals in an oxidation alkali medium; for decreasing and/or preventing color deviation in the hair, and/or chromaticity deviation, and/or hair damage provoked by a ready-to-use hair dyeing, and/or bleaching composition comprising at least one oxidant.

In a seventh aspect, the method for dyeing and/or bleaching hair, which comprises applying to the hair a composition comprising a cosmetically effective amount of at least one chelating agent dissolved in a water-based medium, suitable for chelating cationic transition metals in an oxidation alkali medium; at least one hair oxidative dyeing or bleaching agent; at least one oxidant, and wherein the composition is a ready-to-use hair dyeing and/or bleaching composition having an alkaline pH, and rinsing the hair with water after an application time of the ready-to-use hair dyeing and/or bleaching composition in the hair from 1 minute to 1 hour.

In an eighth aspect, the method for dyeing and/or bleaching hair, which comprises a) applying to the hair a composition having an alkaline pH and comprising an effective amount of at least one chelating agent, suitable for chelating cationic transition metals in an oxidation alkali medium, b) optionally rinsing the hair, c) optionally drying the hair, and d) applying a ready-to-use hair dyeing and/or bleaching composition comprising at least one hair oxidative dyeing or bleaching agent, and at least one oxidant, and rinsing the hair with water after an application time of the ready-to-use hair dyeing and/or bleaching composition in the hair from 1 minute to 1 hour.

In an ninth aspect, the method for hair cosmetic treatment, which comprises a method for dyeing and/or bleaching hair, which comprises applying to the hair a composition comprising a cosmetically effective amount of at least one chelating agent dissolved in water, suitable for chelating cationic transition metals in an oxidation alkali medium; at least one hair oxidative dyeing or bleaching agent; at least one oxidant, and wherein the composition is a ready-to-use hair dyeing and/or bleaching composition having an alkaline pH, or a method for dyeing and/or bleaching hair, which comprises a) applying to the hair a composition having an alkaline pH and comprising an effective amount of at least one chelating agent, suitable for chelating cationic transition metals in an oxidation alkali medium, b) optionally rinsing the hair, c) optionally drying the hair, and d) applying a ready-to-use hair dyeing and/or bleaching composition comprising at least one hair oxidative dyeing or bleaching agent, and at least one oxidant, and rinsing the hair with water after an application time of the ready-to-use hair dyeing and/or bleaching composition in the hair from 1 minute to 1 hour, and at least one treatment step with at least one hair care product selected from the group of shampoos, conditioners, masks, sprays, oils and/or serums.

DETAILED DESCRIPTION

Embodiments of the present invention are discussed in detail below. In describing embodiments, specific terminology is employed for the sake of clarity. However, the invention is not intended to be limited to the specific terminology so selected. While specific exemplary embodiments are discussed, it should be understood that this is done for illustration purposes only. A person skilled in the relevant art will recognize that other components and configurations can be used without parting from the spirit and scope of the invention. While a number of embodiments and features are described herein, it is to be understood that the various features of the invention and aspects of embodiments, even if described separately, may be combined unless mutually exclusive or contrary to the specific description. All references cited herein are incorporated by reference as if each had been individually incorporated.

As used herein, the transitional term "comprising," which is synonymous with "including," "containing," or "characterized by," is inclusive or open-ended and does not exclude additional, un-recited elements or method steps. However, in each recitation of "comprising" herein, it is intended that the term also encompass, as alternative embodiments, the phrases "consisting essentially of" and "consisting of", where "consisting of" excludes any element or step not specified and "consisting essentially of" permits the inclusion of additional un-recited elements or steps that do not materially affect the essential or basic and novel characteristics of the composition or method under consideration.

The present disclosure relates to a composition having an alkaline pH and comprising an effective amount of at least one chelating agent, suitable for chelating cationic transition metals in an oxidation alkali medium.

This composition prevents or minimizes the hair damage by free radicals, color deviation in the hair, or chromaticity deviation in permanent oxidative hair dyeing and/or bleaching treatments, as it is shown in the non-limiting examples.

In this disclosure, "hair" means keratin fibers that grow on the scalp.

In this disclosure, "hair damage by free radicals" is the degradation of protein keratin fibers in the inner structure of the hair provoked by free radicals. Hair damage is measured by the concentration of tryptophan by steady state fluorescence.

In the present disclosure, "color deviation" is the color difference between two measurements by solid phase spectrophotometry, where according to the formula $\Delta E = \sqrt{(L_1-L_0)^2+(a_1-a_0)^2+(b_1-b_0)^2}$, CIE76 (Commission internationale de l'éclairage, formula from 1976) the difference is higher than 2.0 units, what corresponds to a JND (just noticeable difference). "Color deviation in the hair" means that the color deviation between dyed hair without pollutant cationic metals and dyed hair containing pollutant cationic metals is higher than 2.0 units, and the color deviation between dyed hair without pollutant cationic metals and dyed hair containing pollutant cationic metals, but treated with the composition of the present disclosure, is lower than or equal to 2.0 units, and it is not JND.

Color chromaticity is a color parameter based in the color measurements by solid phase spectrophotometry in a CIELab space without the luminance component, according to the formula: $C=\sqrt{a^2+b^2}$. In the present disclosure, "chromaticity deviation" is a modulus from the difference between two color chromaticities higher than 2.0 units, what corresponds to a JND. "Chromaticity deviation in the hair" means that the chromaticity deviation between dyed hair without pollutant cationic metals and dyed hair containing pollutant cationic metals is higher than 2.0 units, and the chromaticity deviation between dyed hair without pollutant cationic metals and dyed hair containing pollutant cationic metals, but treated with the composition of the present disclosure, is lower than or equal to 2.0 units, and it is not JND.

Alkaline pH is a pH above 7. Alkali medium is a medium having a pH above 7. In one non-limiting embodiment, the pH of the above disclosed composition and/or the pH of the alkali medium may be above 8 and below 12.

Oxidation medium is a medium containing at least one oxidant. The oxidant may be a peroxide compound, an inorganic peroxide, or hydrogen peroxide. An "oxidant" is a compound that undergoes a chemical reaction that removes one or more electrons from other reactants.

Transition metals are defined as elements from the groups 4 to 12 of the periodic table and scandium and yttrium. Oxidation states for cationic transition metals may include for example, but are not limited to, $Cu^{2+}$, $Fe^{2+}$, $Fe^{3+}$, $Co^{2+}$, $Co^{3+}$, $Zn^{2+}$, $Mn^{2+}$, $Ni^{2+}$, $Cr^{2+}$, $Ag^+$, $Cu^+$, $Cd^{2+}$, $Hg^{2+}$, or $Sc^{3+}$.

For purposes of this disclosure, "effective amount" or "cosmetically effective amount" are understood to mean a nontoxic but sufficient amount of the ingredients of the composition to provide the desired effect. The ingredients are used in the composition at cosmetically effective concentrations to achieve the desired effect.

The composition having an alkaline pH and comprising an effective amount of at least one chelating agent, suitable for chelating cationic transition metals in an oxidation alkali medium may be a water-based composition. The composition having an alkaline pH and comprising an effective amount of at least one chelating agent, suitable for chelating cationic transition metals in an oxidation alkali medium may be a cosmetic composition, or a hair cosmetic composition. The composition having an alkaline pH and comprising an effective amount of at least one chelating agent, suitable for chelating cationic transition metals in an oxidation alkali medium may be a water-based cosmetic composition or a water-based hair cosmetic composition. For purposes of this disclosure, "water-based" is understood to mean a composition or medium in the form of water solution, hydroalcoholic solution, hydroglycolic solution, o/w emulsion, w/o emulsion, w/o/w emulsion, o/w/o emulsion or hydrogel, wherein the content of water may be higher than 40%, higher than 50%, or higher than 60% by weight based on the total weight of the composition. The hair cosmetic composition may be a serum, a rinse-off hair conditioner, a rinse-off hair mask, a leave-on hair conditioner, a leave-on hair mask or a spray. The composition may take the form of a booster to be added to other compositions, or cosmetic compositions, or hair cosmetic compositions. A "rinse off" conditioner or mask is a conditioner or mask washed off with water and not left on the hair after the application time. A "leave on" conditioner or mask is a conditioner or mask which is intended to stay in prolonged contact with the hair.

The chelating agent in the composition is dissolved. The terms "solved" or "dissolved" herein refers that all effective amount of the chelating agent is no longer in powder or crystal form in the composition or medium, or water-based composition or water-based medium.

The effective amount of the at least one chelating agent may range from 0.1%, or from 0.2%, or from 0.5%, or from 1%, or from 2%, or from 4.36%, or from 5% by weight based on the total weight of the composition to the saturation value of the chelating agent in the composition. The chelating agent may be dissolved in the water-based composition.

In this disclosure, "saturation value" of the chelating agent in the composition means the concentration of chelating agent at which, or above which the chelating agent precipitates out in the composition. This composition may be a water-based composition. This composition may be a cosmetic composition, or a hair cosmetic composition. The water-based composition may be a water-based cosmetic composition or a water-based hair cosmetic composition.

The effective amount of chelating agent may range from 0.1%, or from 0.2%, or from 0.5%, or from 1%, or from 2%, or from 4.36%, or from 5% by weight based on the total weight of the composition to the saturation value of the chelating agent in the composition. The chelating agent in the composition, suitable for chelating cationic transition metals in an oxidation alkali medium, may be a mixture of at least one alkali and/or alkaline earth metal salt of diethylenetriamine pentaacetic acid, and at least one alkali metal salt of etidronic acid, wherein the effective amount for the mixture of salts may range from 0.1%, or from 0.2%, or from 0.5%, or from 1%, or from 2%, or from 4.36%, or from 5% by weight based on the total weight of the composition to the saturation value of the chelating agent in the composition.

The chelating agent in the composition, suitable for chelating cationic transition metals in an oxidation alkali medium, may be at least one salt of nitrilotriacetic acid, a salt of etidronic acid, a salt of pentetic acid, a salt of ethylenediamine tetramethylene phosphonic acid, a salt of aminotrimethylene phosphonic acid, a salt of N,N'-ethylenediamine disuccinic acid, a salt of hexamethylenediamine tetra(methylenephosphonic acid), a salt of diethylenetriamine pentamethylene phosphonic acid, or a mixture thereof. This composition may be a water-based composition. This composition may be a cosmetic composition, or a hair cosmetic composition. The water-based composition may be a water-based cosmetic composition or a water-based hair cosmetic composition. The chelating agent in the composition, suitable for chelating cationic transition metals in an oxidation alkali medium, may be at least one salt of diethylenetriamine pentaacetic acid, or at least one salt of etidronic acid, or a mixture thereof. This composition may be a water-based composition. This composition may be a cosmetic composition, or a hair cosmetic composition. The water-based composition may be a water-based cosmetic composition or a water-based hair cosmetic composition. The salt of diethylenetriamine pentaacetic acid may be an alkali and/or alkaline earth metal salt of diethylenetriamine pentaacetic acid. The alkali and/or alkaline earth metal salt of diethylenetriamine pentaacetic acid may be pentasodium pentetate, calcium trisodium pentetate and potassium pentetate. The salt of etidronic acid may be an alkali metal salt of etidronic acid. The alkali metal salt of etidronic acid may be disodium etidronate, tetrasodium etidronate and tetrapotassium etidronate. The chelating agent in the composition, suitable for chelating cationic transition metals in an oxidation alkali medium, may be a mixture of at least one alkali and/or alkaline earth metal salt of diethylenetriamine pentaacetic acid, and at least one alkali metal salt of etidronic acid. This composition may be a water-based composition. This composition may be a cosmetic composition, or a hair cosmetic composition. The water-based composition may be a water-based cosmetic composition or a water-based hair cosmetic composition. The chelating agent in the composition, suitable for chelating cationic transition metals in an oxidation alkali medium, may be a mixture of at least one salt selected from pentasodium pentetate, calcium trisodium pentetate and potassium pentetate, and at least one salt selected from disodium etidronate, tetrasodium etidronate and tetrapotassium etidronate. This composition may be a water-based composition. This composition may be a cosmetic composition, or a hair cosmetic composition. The water-based composition may be a water-based cosmetic composition or a water-based hair cosmetic composition. The chelating agent in the composition, suitable for chelating cationic transition metals in an oxidation alkali medium, may be a mixture of at least pentasodium pentetate and tetrasodium etidronate. This composition may be a water-based composition. This composition may be a cosmetic composition, or a hair cosmetic composition. The water-based composition may be a water-based cosmetic composition or a water-based hair cosmetic composition.

The chelating agent in the composition, suitable for chelating cationic transition metals in an oxidation alkali medium, may be a mixture of at least one salt of etidronic acid and at least one salt of diethylenetriamine pentaacetic acid, wherein the molar ratio of the at least one salt of etidronic acid versus the at least one salt of diethylenetriamine pentaacetic acid may range from 10:1 to 1:5, or from 10:1 to 1:2, or from 10:1 to 1:1, or from 10:1 to 1.2:1, or from 10:1 to 1.5:1, or from 7:1 to 1:2, or from 7:1 to 1:1, or from 7:1 to 1.2:1, or from 7:1 to 1.5:1, or from 5:1 to 1:2, or from 5:1 to 1:1, or from 5:1 to 1.2:1, or from 5:1 to 1.5:1, or from 4:1 to 1:2, or from 4:1 to 1:1, or from 4:1 to 1.2:1, or from 4:1 to 1.5:1, or from 3:1 to 1:2, or from 3:1 to 1:1, or from 3:1 to 1.2:1, or from 3:1 to 1.5:1. This composition may be a water-based composition. This composition may be a cosmetic composition, or a hair cosmetic composition. The water-based composition may be a water-based cosmetic composition or a water-based hair cosmetic composition. The salt of diethylenetriamine pentaacetic acid may be an alkali and/or alkaline earth metal salt of diethylenetriamine pentaacetic acid. The alkali and/or alkaline earth metal salt of diethylenetriamine pentaacetic acid may be pentasodium pentetate, calcium trisodium pentetate and potassium pentetate. The salt of etidronic acid may be an alkali metal salt of etidronic acid. The alkali metal salt of etidronic acid may be disodium etidronate, tetrasodium etidronate and tetrapotassium etidronate. The chelating agent in the composition, suitable for chelating cationic transition metals in an oxidation alkali medium, may be a mixture of at least one alkali and/or alkaline earth metal salt of diethylenetriamine pentaacetic acid, and at least one alkali metal salt of etidronic acid, wherein the molar ratio of the at least one alkali metal salt of etidronic acid versus the at least one alkali and/or alkaline earth metal salt of diethylenetriamine pentaacetic acid may range from 10:1 to 1:5, or from 10:1 to 1:2, or from 10:1 to 1:1, or from 10:1 to 1.2:1, or from 10:1 to 1.5:1, or from 7:1 to 1:2, or from 7:1 to 1:1, or from 7:1 to 1.2:1, or from 7:1 to 1.5:1, or from 5:1 to 1:2, or from 5:1 to 1:1, or from 5:1 to 1.2:1, or from 5:1 to 1.5:1, or from 4:1 to 1:2, or from 4:1 to 1:1, or from 4:1 to 1.2:1, or from 4:1 to 1.5:1, or from 3:1 to 1:2, or from 3:1 to 1:1, or from 3:1 to 1.2:1, or from 3:1 to 1.5:1. This composition may be a water-based composition. This composition may be a cosmetic composition, or a hair cosmetic composition. The water-based composition may be a water-based cosmetic composition or a water-based hair cosmetic composition. The chelating agent in the composition, suitable for chelating cationic transition metals in an oxidation alkali medium, may be a mixture of at least one salt selected from pentasodium pentetate, calcium trisodium pentetate and potassium pentetate, and at least one salt selected from disodium etidronate, tetrasodium etidronate and tetrapotassium etidronate, wherein the molar ratio of the at least one etidronate salt versus the at least one pentetate salt may range from 10:1 to 1:5, or from 10:1 to 1:2, or from 10:1 to 1:1, or from 10:1 to 1.2:1, or from 10:1 to 1.5:1, or from 7:1 to 1:2, or from 7:1 to 1:1, or from 7:1 to 1.2:1, or from 7:1 to 1.5:1, or from 5:1 to 1:2, or from 5:1 to 1:1, or from 5:1 to 1.2:1, or from 5:1 to 1.5:1, or from 4:1 to 1:2, or from 4:1 to 1:1, or from 4:1 to 1.2:1, or from 4:1 to 1.5:1, or from 3:1 to 1:2, or from 3:1 to 1:1, or from 3:1 to 1.2:1, or from 3:1 to 1.5:1. This composition may be a water-based composition. This composition may be a cosmetic composition, or a hair cosmetic composition. The water-based composition may be a water-based cosmetic composition or a water-based hair cosmetic composition. The chelating agent in the composition, suitable for chelating cationic transition metals in an oxidation alkali medium, may be a mixture of at least pentasodium pentetate and tetrasodium etidronate, wherein the molar ratio of the tetrasodium etidronate salt versus the pentasodium pentetate salt may range from 10:1 to 1:5, or from 10:1 to 1:2, or from 10:1 to 1:1, or from 10:1 to 1.2:1, or from 10:1 to 1.5:1, or from 7:1 to 1:2, or from 7:1 to 1:1, or from 7:1 to 1.2:1, or from 7:1 to 1.5:1, or from 5:1 to 1:2, or from 5:1 to 1:1, or from 5:1 to 1.2:1, or from 5:1 to 1.5:1, or from 4:1 to 1:2, or from 4:1 to 1:1, or from 4:1 to 1.2:1, or from 4:1 to 1.5:1, or from 3:1 to 1:2, or from 3:1 to 1:1, or from 3:1 to 1.2:1, or from 3:1 to 1.5:1. This composition may be a water-based composition. This composition may be a cosmetic composition, or a hair cosmetic composition. The water-based composition may be a water-based cosmetic composition or a water-based hair cosmetic composition.

The chelating agent in the composition, suitable for chelating cationic transition metals in an oxidation alkali medium, may be at least one salt of diethylenetriamine pentaacetic acid, or at least one salt of etidronic acid, or a mixture thereof, wherein the effective amount of chelating agent may range from 0.1%, or from 0.2%, or from 0.5%, or from 1%, or from 2%, or from 4.36%, or from 5% by weight based on the total weight of the composition to the saturation value of the chelating agent in the composition. This composition may be a water-based composition. This composition may be a cosmetic composition, or a hair cosmetic composition. The water-based composition may be a water-based cosmetic composition or a water-based hair cosmetic composition. The salt of diethylenetriamine pentaacetic acid may be an alkali and/or alkaline earth metal salt of diethylenetriamine pentaacetic acid. The alkali and/or alkaline earth metal salt of diethylenetriamine pentaacetic acid may be pentasodium pentetate, calcium trisodium pentetate and potassium pentetate. The salt of etidronic acid may be an alkali metal salt of etidronic acid. The alkali metal salt of etidronic acid may be disodium etidronate, tetrasodium etidronate and tetrapotassium etidronate. The chelating agent in the composition, suitable for chelating cationic transition metals in an oxidation alkali medium, may be a mixture of at least one alkali and/or alkaline earth metal salt of diethylenetriamine pentaacetic acid, and at least one alkali metal salt of etidronic acid, wherein the effective amount for the mixture of salts may range from 0.1%, or from 0.2%, or from 0.5%, or from 1%, or from 2%, or from 4.36%, or from 5% by weight based on the total weight of the composition to the saturation value of the chelating agent in the composition. This composition may be a water-based composition. This composition may be a cosmetic composition, or a hair cosmetic composition. The water-based composition may be a water-based cosmetic composition or a water-based hair cosmetic composition. The chelating agent in the composition, suitable for chelating cationic transition metals in an oxidation alkali medium, may be a mixture of at least one salt selected from pentasodium pentetate, calcium trisodium pentetate and potassium pentetate, and at least one salt selected from disodium etidronate, tetrasodium etidronate and tetrapotassium etidronate, wherein the effective amount for the mixture of salts may range from 0.1%, or from 0.2%, or from 0.5%, or from 1%, or from 2%, or from 4.36%, or from 5% by weight based on the total weight of the composition to the saturation value of the chelating agent in the composition. This composition may be a water-based composition. This composition may be a cosmetic composition, or a hair cosmetic composition. The water-based composition may be a water-based cosmetic composition or a water-based hair cosmetic composition. The chelating agent in the composition, suitable for chelating cationic transition metals in an oxidation alkali medium, may be a mixture of at least pentasodium pentetate and tetrasodium etidronate, wherein the effective amount for the mixture of pentasodium pentetate and tetrasodium etidronate may range from 0.1%, or from 0.2%, or from 0.5%, or from 1%, or from 2%, or from 4.36%, or from 5% by weight based on the total weight of the composition to the saturation value of the chelating agent in the composition. This composition may be a water-based composition. This composition may be a cosmetic composition, or a hair cosmetic composition. The water-based composition may be a water-based cosmetic composition or a water-based hair cosmetic composition.

The chelating agent in the composition, suitable for chelating cationic transition metals in an oxidation alkali medium, may be a mixture of at least one salt of etidronic acid and at least one salt of diethylenetriamine pentaacetic acid, wherein the molar ratio of the at least one salt of etidronic acid versus the at least one salt of diethylenetriamine pentaacetic acid may range from 10:1 to 1:5, or from 10:1 to 1:2, or from 10:1 to 1:1, or from 10:1 to 1.2:1, or from 10:1 to 1.5:1, or from 7:1 to 1:2, or from 7:1 to 1:1, or from 7:1 to 1.2:1, or from 7:1 to 1.5:1, or from 5:1 to 1:2, or from 5:1 to 1:1, or from 5:1 to 1.2:1, or from 5:1 to 1.5:1, or from 4:1 to 1:2, or from 4:1 to 1:1, or from 4:1 to 1.2:1, or from 4:1 to 1.5:1, or from 3:1 to 1:2, or from 3:1 to 1:1, or from 3:1 to 1.2:1, or from 3:1 to 1.5:1, and wherein the effective amount of chelating agent may range from 0.1%, or from 0.2%, or from 0.5%, or from 1%, or from 2%, or from 4.36%, or from 5% by weight based on the total weight of the composition to the saturation value of the chelating agent in the composition. This composition may be a water-based composition. This composition may be a cosmetic composition, or a hair cosmetic composition. The water-based composition may be a water-based cosmetic composition or a water-based hair cosmetic composition. The salt of diethylenetriamine pentaacetic acid may be an alkali and/or alkaline earth metal salt of diethylenetriamine pentaacetic acid. The alkali and/or alkaline earth metal salt of diethylenetriamine pentaacetic acid may be pentasodium pentetate, calcium trisodium pentetate and potassium pentetate. The salt of etidronic acid may be an alkali metal salt of etidronic acid. The alkali metal salt of etidronic acid may be disodium etidronate, tetrasodium etidronate and tetrapotassium etidronate. The chelating agent in the composition, suitable for chelating cationic transition metals in an oxidation alkali medium, may be a mixture of at least one alkali and/or alkaline earth metal salt of diethylenetriamine pentaacetic acid, and at least one alkali metal salt of etidronic acid, wherein the molar ratio of the at least one alkali metal salt of etidronic acid versus the at least one alkali and/or alkaline earth metal salt of diethylenetriamine pentaacetic acid may range from 10:1 to 1:5, or from 10:1 to 1:2, or from 10:1 to 1:1, or from 10:1 to 1.2:1, or from 10:1 to 1.5:1, or from 7:1 to 1:2, or from 7:1 to 1:1, or from 7:1 to 1.2:1, or from 7:1 to 1.5:1, or from 5:1 to 1:2, or from 5:1 to 1:1, or from 5:1 to 1.2:1, or from 5:1 to 1.5:1, or from 4:1 to 1:2, or from 4:1 to 1:1, or from 4:1 to 1.2:1, or from 4:1 to 1.5:1, or from 3:1 to 1:2, or from 3:1 to 1:1, or from 3:1 to 1.2:1, or from 3:1 to 1.5:1, and wherein the effective amount for the mixture of salts may range from 0.1%, or from 0.2%, or from 0.5%, or from 1%, or from 2%, or from 4.36%, or from 5% by weight based on the total weight of the composition to the saturation value of the chelating agent in the composition. This composition may be a water-based composition. This composition may be a cosmetic composition, or a hair cosmetic composition. The water-based composition may be a water-based cosmetic composition or a water-based hair cosmetic composition. The chelating agent in the composition, suitable for chelating cationic transition metals in an oxidation alkali medium, may be a mixture of at least one salt selected from pentasodium pentetate, calcium trisodium pentetate and potassium pentetate, and at least one salt selected from disodium etidronate, tetrasodium etidronate and tetrapotassium etidronate, wherein the molar ratio of the at least one etidronate salt versus the at least one pentetate salt may range from 10:1 to 1:5, or from 10:1 to 1:2, or from 10:1 to 1:1, or from 10:1 to 1.2:1, or from 10:1 to 1.5:1, or from 7:1 to 1:2, or from 7:1 to 1:1, or from 7:1 to 1.2:1, or from 7:1 to 1.5:1, or from 5:1 to 1:2, or from 5:1 to 1:1, or from 5:1 to 1.2:1, or from 5:1 to 1.5:1, or from 4:1 to 1:2, or from 4:1 to 1:1, or from 4:1 to 1.2:1, or from 4:1 to 1.5:1, or from 3:1 to 1:2, or from 3:1 to 1:1, or from 3:1 to 1.2:1, or from 3:1 to 1.5:1, and wherein the effective amount for the mixture of salts may range from 0.1%, or from 0.2%, or from 0.5%, or from 1%, or from 2%, or from 4.36%, or from 5% by weight based on the total weight of the composition to the saturation value of the chelating agent in the composition. This composition may be a water-based composition. This composition may be a cosmetic composition, or a hair cosmetic composition. The water-based composition may be a water-based cosmetic composition or a water-based hair cosmetic composition. The chelating agent in the composition, suitable for chelating cationic transition metals in an oxidation alkali medium, may be a mixture of at least pentasodium pentetate and tetrasodium etidronate, wherein the molar ratio of the tetrasodium etidronate salt versus the pentasodium pentetate salt may range from 10:1 to 1:5, or from 10:1 to 1:2, or from 10:1 to 1:1, or from 10:1 to 1.2:1, or from 10:1 to 1.5:1, or from 7:1 to 1:2, or from 7:1 to 1:1, or from 7:1 to 1.2:1, or from 7:1 to 1.5:1, or from 5:1 to 1:2, or from 5:1 to 1:1, or from 5:1 to 1.2:1, or from 5:1 to 1.5:1, or from 4:1 to 1:2, or from 4:1 to 1:1, or from 4:1 to 1.2:1, or from 4:1 to 1.5:1, or from 3:1 to 1:2, or from 3:1 to 1:1, or from 3:1 to 1.2:1, or from 3:1 to 1.5:1, and wherein the effective amount for the mixture of pentasodium pentetate and tetrasodium etidronate may range from 0.1%, or from 0.2%, or from 0.5%, or from 1%, or from 2%, or from 4.36%, or from 5% by weight based on the total weight of the composition to the saturation value of the chelating agent in the composition. This composition may be a water-based composition. This composition may be a cosmetic composition, or a hair cosmetic composition. The water-based composition may be a water-based cosmetic composition or a water-based hair cosmetic composition.

The chelating agent in the composition, suitable for chelating cationic transition metals in an oxidation alkali medium, may be a mixture of at least one salt of etidronic acid and at least one salt of diethylenetriamine pentaacetic acid, wherein the molar ratio of the at least one salt of etidronic acid versus the at least one salt of diethylenetriamine pentaacetic acid may range from 10:1 to 1:5, or from 10:1 to 1:2, or from 10:1 to 1:1, or from 10:1 to 1.2:1, or from 10:1 to 1.5:1, or from 7:1 to 1:2, or from 7:1 to 1:1, or from 7:1 to 1.2:1, or from 7:1 to 1.5:1, or from 5:1 to 1:2, or from 5:1 to 1:1, or from 5:1 to 1.2:1, or from 5:1 to 1.5:1, or from 4:1 to 1:2, or from 4:1 to 1:1, or from 4:1 to 1.2:1, or from 4:1 to 1.5:1, or from 3:1 to 1:2, or from 3:1 to 1:1, or from 3:1 to 1.2:1, or from 3:1 to 1.5:1, and wherein the effective amount of chelating agent may range from 4.36% by weight based on the total weight of the composition to the saturation value of the chelating agent in the composition. This composition may be a water-based composition. This composition may be a cosmetic composition, or a hair cosmetic composition. The water-based composition may be a water-based cosmetic composition or a water-based hair cosmetic composition. The salt of diethylenetriamine pentaacetic acid may be an alkali and/or alkaline earth metal salt of diethylenetriamine pentaacetic acid. The alkali and/or alkaline earth metal salt of diethylenetriamine pentaacetic acid may be pentasodium pentetate, calcium trisodium pentetate and potassium pentetate. The salt of etidronic acid may be an alkali metal salt of etidronic acid. The alkali metal salt of etidronic acid may be disodium etidronate, tetrasodium etidronate and tetrapotassium etidronate. The chelating agent in the composition, suitable for chelating cationic transition metals in an oxidation alkali medium, may be a mixture of at least one alkali and/or alkaline earth metal salt of diethylenetriamine pentaacetic acid, and at least one alkali metal salt of etidronic acid, wherein the molar ratio of the at least one alkali metal salt of etidronic acid versus the at least one alkali and/or alkaline earth metal salt of diethylenetriamine pentaacetic acid may range from 10:1 to 1:5, or from 10:1 to 1:2, or from 10:1 to 1:1, or from 10:1 to 1.2:1, or from 10:1 to 1.5:1, or from 7:1 to 1:2, or from 7:1 to 1:1, or from 7:1 to 1.2:1, or from 7:1 to 1.5:1, or from 5:1 to 1:2, or from 5:1 to 1:1, or from 5:1 to 1.2:1, or from 5:1 to 1.5:1, or from 4:1 to 1:2, or from 4:1 to 1:1, or from 4:1 to 1.2:1, or from 4:1 to 1.5:1, or from 3:1 to 1:2, or from 3:1 to 1:1, or from 3:1 to 1.2:1, or from 3:1 to 1.5:1, and wherein the effective amount for the mixture of salts may range from 4.36% by weight based on the total weight of the composition to the saturation value of the chelating agent in the composition. This composition may be a water-based composition. This composition may be a cosmetic composition, or a hair cosmetic composition. The water-based composition may be a water-based cosmetic composition or a water-based hair cosmetic composition. The chelating agent in the composition, suitable for chelating cationic transition metals in an oxidation alkali medium, may be a mixture of at least one salt selected from pentasodium pentetate, calcium trisodium pentetate and potassium pentetate, and at least one salt selected from disodium etidronate, tetrasodium etidronate and tetrapotassium etidronate, wherein the molar ratio of the at least one etidronate salt versus the at least one pentetate salt may range from 10:1 to 1:5, or from 10:1 to 1:2, or from 10:1 to 1:1, or from 10:1 to 1.2:1, or from 10:1 to 1.5:1, or from 7:1 to 1:2, or from 7:1 to 1:1, or from 7:1 to 1.2:1, or from 7:1 to 1.5:1, or from 5:1 to 1:2, or from 5:1 to 1:1, or from 5:1 to 1.2:1, or from 5:1 to 1.5:1, or from 4:1 to 1:2, or from 4:1 to 1:1, or from 4:1 to 1.2:1, or from 4:1 to 1.5:1, or from 3:1 to 1:2, or from 3:1 to 1:1, or from 3:1 to 1.2:1, or from 3:1 to 1.5:1, and wherein the effective amount for the mixture of salts may range from 4.36% by weight based on the total weight of the composition to the saturation value of the chelating agent in the composition. This composition may be a water-based composition. This composition may be a cosmetic composition, or a hair cosmetic composition. The water-based composition may be a water-based cosmetic composition or a water-based hair cosmetic composition. The chelating agent in the composition, suitable for chelating cationic transition metals in an oxidation alkali medium, may be a mixture of at least pentasodium pentetate and tetrasodium etidronate, wherein the molar ratio of the tetrasodium etidronate salt versus the pentasodium pentetate salt may range from 10:1 to 1:5, or from 10:1 to 1:2, or from 10:1 to 1:1, or from 10:1 to 1.2:1, or from 10:1 to 1.5:1, or from 7:1 to 1:2, or from 7:1 to 1:1, or from 7:1 to 1.2:1, or from 7:1 to 1.5:1, or from 5:1 to 1:2, or from 5:1 to 1:1, or from 5:1 to 1.2:1, or from 5:1 to 1.5:1, or from 4:1 to 1:2, or from 4:1 to 1:1, or from 4:1 to 1.2:1, or from 4:1 to 1.5:1, or from 3:1 to 1:2, or from 3:1 to 1:1, or from 3:1 to 1.2:1, or from 3:1 to 1.5:1, and wherein the effective amount for the mixture of pentasodium pentetate and tetrasodium etidronate may range from 4.36% by weight based on the total weight of the composition to the saturation value of the chelating agent in the composition. This composition may be a water-based composition. This composition may be a cosmetic composition, or a hair cosmetic composition. The water-based composition may be a water-based cosmetic composition or a water-based hair cosmetic composition.

The composition having an alkaline pH and comprising an effective amount of at least one chelating agent, suitable for chelating cationic transition metals in an oxidation alkali medium, may be a water-based composition, or may be a cosmetic composition, or a hair cosmetic composition, or may be a water-based cosmetic composition or a water-based hair cosmetic composition and the composition may comprise at least one additional cosmetic ingredient selected from the group of hair strengtheners, free radical scavengers, humectants, emollients, emulsifiers, viscosity increasing ingredients, thickeners, bulking agents, solvents, emulsion stabilizers, hair conditioners, natural extracts, antioxidants, pH adjusters, hair fixatives, film formers, UV filters, opacifying agents, fragrance ingredients, preservatives and cosmetic colorants.

In this disclosure, "hair strengtheners" are compounds that improve the resistance to hair breakage.

In this disclosure, "free radical scavengers" are substances that capture free radicals, such as Reactive Oxygen Species (ROS), Reactive Nitrogen Species (RNS) or Reactive Carbon Species (RCS), in order to avoid harmful effects on the skin, scalp and/or hair.

In this disclosure, "humectants" are ingredients used in cosmetic products to retard moisture loss from the product during use.

In this disclosure, "emollients" are cosmetic ingredients which help to maintain the soft, smooth, and pliable appearance of hair, and they act as lubricants.

In this disclosure, "emulsifiers" are cosmetic ingredients required for the formation of emulsions that stabilize an emulsion by increasing its kinetic stability.

In this disclosure, "viscosity increasing agents" are cosmetic ingredients used to thicken cosmetic products.

In this disclosure, "bulking agents" are cosmetic ingredients used to increase the volume of a cosmetic.

In this disclosure, "solvents" are liquids employed to dissolve components found useful in cosmetics.

In this disclosure, "emulsion stabilizers" are cosmetic ingredients that assist in the formation and the stabilization of emulsions. Emulsion stabilizers do not act as primary emulsifiers, but prevent or reduce the coalescence of emulsified droplets, and they enhance the activity of emulsifiers.

In this disclosure, "hair conditioners" are ingredients used to create special effects on hair, and they include ingredients which enhance the appearance and feel of hair, increase hair body or suppleness, facilitate styling, improve gloss or sheen and improve the texture of hair, including hair that has been damaged by chemical or physical action.

In this disclosure, "natural extracts" are substances or active ingredients with desirable properties that are removed from a plant, flower, alga, fungus or bacteria, usually by treating it with a solvent, to be used for a particular purpose.

In this disclosure, "antioxidants" are ingredients employed in cosmetics to prevent or retard product spoilage from rancidity or deterioration from reaction with oxygen, they play a vital role in maintaining the quality, integrity, and safety of cosmetic products.

In this disclosure, "pH adjusters" are acids, bases, or buffering agents which are used to control the pH of cosmetic products or ingredients.

In this disclosure, "hair fixatives" are ingredients which impart holding or style-retention properties to hair.

In this disclosure, "film formers" are ingredients which produce a continuous film on hair.

In this disclosure, "UV filters" are ingredients used to absorb or reflect the UV rays that are contained in sun light or in artificial light, they can be used to protect the skin from the harmful effects of UV light or to protect cosmetic products and ingredients.

In this disclosure, "opacifying agents" are ingredients deliberately added to cosmetic products to reduce their clear or transparent appearance.

In this disclosure, "fragrance ingredients" are any natural or synthetic substance or substances used to impart an odor to a cosmetic product.

In this disclosure, "preservatives" are ingredients which prevent or retard microbial growth and thus protect cosmetic products from spoilage, they also protect the product from inadvertent contamination by the consumer during use.

In this disclosure, "cosmetic colorants" are cosmetic ingredients which impart color to finished products, but do not change the color or tone of hair, based on visual inspection, and therefore, they are different from the hair oxidative dyeing agents.

The composition having an alkaline pH and comprising an effective amount of at least one chelating agent, suitable for chelating cationic transition metals in an oxidation alkali medium, may be a water-based composition, or may be a cosmetic composition, or a hair cosmetic composition, or may be a water-based cosmetic composition or a water-based hair cosmetic composition and the composition may include, but is not limited to, at least one hair strengthener, and/or at least one free radical scavenger. The hair strengthener may be selected, for example and not restricted to, from the group formed by Cystine Bis-PG-Propyl Silanetriol, Hydroxypropylgluconamide, creatine, sage essential oil, rosemary essential oil, peppermint essential oil, Keravis [INCI: Hydrolyzed Vegetable Protein PG-Propyl Silanetriol] marketed by Sederma/Croda, phytosterols, isoflavones, soya isoflavones, retinol, zinc and derivatives thereof, neoruscine, vitamin E, vitamin B2, vitamin B3, vitamin B6, vitamin PP, vitamin B5 (panthenol), vitamin B8 (biotin), vitamin B9 (folic acid), alpha hydroxy acid, quinine and certain sulfur-containing amino acids such as cysteine, cystine and methionine, *Serenoa serrulata* or *repens* extract, *Cucurbita pepo* extract, keratin, *Pfaffia* oil extract, lemon, ginseng, quinquina, jojoba, horse chestnut, honey, wheat, nettle, echinea, cophra or coconut extracts. The free radical scavenger may be selected, for example and not restricted to, from the group formed by carnosine and its derivatives, arginine, histidine, lysine, nicorandil, sesamin, GHK [INCI: Tripeptide-1] and its salts and/or derivatives, Quintescine IS [INCI: Dipeptide-4] marketed by Vincience/ISP/Ashland; Melitane [INCI: Dextran, Acetyl Hexapeptide-1], Homeoxy [INCI: *Enteromorpha Compressa, Palmaria Palmata* Extract] or Lanatellis [INCI: Glycerin, Aqua, *Chrysantellum Indicum* Extract, *Camellia Sinensis* Leaf Extract] marketed by Atrium Innovations/Lucas Meyer Cosmetics; Protectan [INCI: *Lactococcus* Ferment Lysate] marketed by CLR; Phycosaccharide [INCI: Water, Hydrolysed Algin, Magnesium Sulfate, Manganese Sulfate] or Algowhite [INCI: Water, *Ascophyllum Nodosum* Extract] marketed by Codif; Preregen [INCI: Glycine Soja (Soybean) Protein, Oxido Reductases], Edelweiss GC [INCI: *Leontopodium Alpinum* Extract], Lipogard [INCI: Squalane, Ubiquinone], Nectapure [INCI: *Buddleja Davidii Extract, Thymus Vulgaris* Extract], Alpaflor Nectapure [INCI: *Buddleja Davidii* Extract, *Thymus Vulgaris* Extract, Glycerin, Water] or Dismutin-BT [INCI: Highly purified SOD from a natural yeast strain of *Saccharomyces cerevisiae*] marketed by Pentapharm/DSM; TEGO Turmerone [INCI: *Curcuma Longa* Extract] marketed by Evonik Goldschmidt; Hierogaline [INCI: *Triticum Vulgare* (Wheat) germ oil unsaponifiables, *Sesamum Indicum* (Sesame) oil unsaponifiables] marketed by Expanscience Laboratoires; Glistin [INCI: Glutamylamidoethyl Indole, Aqua], Glutrapeptide [INCI: Aqua, Pyroglutamylamidoethyl Indole], Algisium C [INCI: Methylsilanol Mannuronate], Silysin C [INCI: Silanetriol Lysinate], Exsy-Arl [INCI: Prolinamidoethyl Imidazole, Butylene Glycol, Aqua] or OTZ-10 [INCI: Aqua, Oxothiazolidine] marketed by Exsymol; Gatuline Skin-Repair Bio [INCI: Alcohol, Water, Onopordum Acanthium Flower/Leaf/Stem extract] marketed by Gattefosse; Preventhelia® [INCI: Diaminopropionoyl Tripeptide-33], Aldenine® [INCI: Hydrolized Wheat Protein, Hydrolized Soy Protein, Tripeptide-1], Lipochroman™ [INCI: Dimethylmethoxy Chromanol], Thermostressine® [INCI: Acetyl Tetrapeptide-22], Juveleven™ [INCI: Acetyl Hexapeptide-51] or Bodyfensine® [INCI: Acetyl Dipeptide-3 Aminohexanoate] marketed by Lipotec/Lubrizol; Setiline [INCI: Hydrolyzed *Trigonella Foenum-Graecum* Seed Extract] marketed by Greentech; Sunactyl [INCI: Mannitol, *Pisum Sativum* Extract, Histidine HCl, Arginine, Cyclodextrin, Dextrin, Yeast Extract, Acetyl Trysoine, Pyridoxine HCl, *Khaya Senegalensis* Bark Extract, Nicotinamide, Adenine Dinucleotide, Disodium Succinate, Aspartic Acid], Imidinyl [INCI: *Tamarindus Indica* Seed Polysaccharide], Phystrogene [INCI: Butylene Glycol, *Malva Sylvestris* (Mallow) Extract, Xanthan Gum] or Purisoft [INCI: *Moringa Pterogysperma* Seed Extract] marketed by Laboratoires Sbrobiologiques/Cognis/BASF; AquaCacteen [INCI: Glycerin, *Opuntia Ficus Indica* Stem Extract, Phenoxyethanol, Aqua], Trimoist (KMF) [INCI: Sodium Stearoyl Lactylate, Letyl alcohol, Vegetable oil, Tocopheryl acetate, Glycerin, Glycine soja sterol, Sodium lactate, Sodium barboxymethyl betaglucan, Carnosine], MelanoBronze [INCI: Vitex Agnus Castus Extract (Monk's pepper berries extract (phyto-endorphins)), Acetyl Tyrosine], CM-Glucan [INCI: Sodium Carboxymethyl Betaglucan, Phenoxyethanol, SunActin [INCI: *Helianthus Annuus* (Sunflower) Sprout Extract, Tocopherols, Glycerin, Lecithin, Phenoxyethanol, Aqua], GSP-T skin [INCI: Glycerin, Alcohol, Aqua, PEG-40 Hydrogenated Castor Oil, *Vitis Vinifera* (Grape) Seed Extract] or Detoxophane [INCI: *Lepidium Sativum* Sprout Extract, Lecithin, Phenoxyethanol, Glycerin, Water] marketed by Mibelle Biochemistry; Bacocalmine [INCI: PEG-8, *Bacopa Monniera* Extract, Water (Aqua), Hydroxyethylcellulose], Kombuchka [INCI: *Saccharomyces/Xylinum* Black Tea Ferment, Glycerin, Hydroxyethyl cellulose] or Prodizia [INCI: *Albizia Julibrissin* Extract, Glycerin] marketed by Sederma/Croda; Extramel C [INCI: Hydroxypropyltrimonium Maltodextrin Crosspolymer, *Cucumis Melo* (Melon) Fruit Extract] marketed by Seppic; Defensine [INCI: *Triticum Vulgare* Germ Extract] or Antiglyskin [INCI: Aqua, *Helianthus Annuus* Seed Extract] marketed by Silab; ATP 23 [INCI: Azeloyl Tetrapeptide-23] marketed by Sinergia; Glycofilm [INCI: Biosaccharide Gum-4] marketed by Solabia. The free radical scavenger may be arginine, histidine, lysine, or Tripeptide-1. The amount of free radical scavengers and/or hair strengtheners in the water-based composition is a cosmetically effective amount to provide the desired effect, and it may range from 0.01% to 30%, from 0.1% to 20%, or from 0.5% to 10%.

The present disclosure also relates to a composition, which comprises a cosmetically effective amount of at least one chelating agent, suitable for chelating cationic transition metals in an oxidation alkali medium; at least one hair oxidative dyeing or bleaching agent; and wherein the composition is a hair dyeing and/or bleaching composition having an alkaline pH.

A "hair oxidative dyeing agent" is an oxidation dye precursor that needs to be activated with hydrogen peroxide in order to provide a coloring effect to the hair. The hair oxidative dyeing agent may be selected, for example and not restricted to, from the group formed by resorcin, 2-methylresorcin, 4-chlororesorcin, 2-chlororesorcin, p-phenylenediamine, toluene-2,5-diamine, p-aminophenol, N,N-bis(2-hydroxyethyl)-p-phenylenediamine, N-phenyl-p-phenylenediamine, 4,4'-diaminodiphenylamine, o-aminophenol, p-methylaminophenol, 2-hydroxyethyl-p-phenylenediamine, o-chloro-p-phenylenediamine, 4-amino-m-cresol, 2-amino-4-hydroxyethylaminoanisole, 2,4-diaminophenol, 1-hydroxyethyl-4,5-diaminopyrazole, m-aminophenol, 5-amino-o-cresol, alpha-naphthol, 2,4-diaminophenoxyethanol, 5-(2-hydroxyethylamino)-2-methylphenol, m-phenylenediamine, toluene-3,4-diamine, 2,6-diaminopyridine diphenylamine, N,N-diethyl-m-aminophenol, phenylmethylpyrazolone, 1,5-dihydroxynaphthalene, derivatives thereof, salts thereof, or mixtures thereof.

A "hair bleaching agent" is an oxidant that needs to be activated with hydrogen peroxide in order to provide a bleaching effect to the hair. For the purposes of the present disclosure, hydrogen peroxide is not a hair bleaching agent.

The hair bleaching agent may be selected, for example and not restricted to, from the group formed by ammonium, alkali and/or alkaline earth metal persulfates, percarbonates, perborates, peroxides, urea peroxide, melamine peroxide and mixtures thereof. The hair bleaching agent may be ammonium persulfate, sodium persulfate, potassium persulfate, sodium percarbonate, potassium percarbonate, sodium perborate, potassium perborate, sodium peroxide, potassium peroxide, magnesium peroxide, barium peroxide, calcium peroxide, strontium peroxide or mixtures thereof. The hair bleaching agent may be sodium persulfate, potassium persulfate, ammonium persulfate or mixtures thereof.

The chelating agent, suitable for chelating cationic transition metals in an oxidation alkali medium, in the hair dyeing and/or bleaching composition is defined equally as the chelating agent, suitable for chelating cationic transition metals in an oxidation alkali medium, in the composition having an alkaline pH. Concentrations, amounts, salts and molar ratios for the chelating agent in this composition, which have been disclosed hereinabove in detail, also apply the chelating agent in the hair dyeing and/or bleaching composition.

The hair dyeing and/or bleaching composition may comprise at least one additional cosmetic ingredient selected from the group of humectants, emollients, emulsifiers, surfactants, viscosity increasing ingredients, thickeners, binders, bulking agents, solvents, emulsion stabilizers, hair conditioners, natural extracts, antioxidants, pH adjusters, hair fixatives, film formers, UV filters, opacifying agents, fragrance ingredients, preservatives and cosmetic colorants.

In this disclosure, "surfactants" are cosmetic ingredients that reduce surface tension of water or reduce the interfacial tension between two immiscible substances.

The present disclosure also relates to a composition, which comprises a cosmetically effective amount of at least one chelating agent dissolved in a water-based medium, suitable for chelating cationic transition metals in an oxidation alkali medium; at least one hair oxidative dyeing or bleaching agent; at least one oxidant, and wherein the composition is a ready-to-use hair dyeing and/or bleaching composition having an alkaline pH.

The oxidant may be hydrogen peroxide.

The chelating agent, suitable for chelating cationic transition metals in an oxidation alkali medium, in the ready-to-use hair dyeing and/or bleaching composition is defined equally as the chelating agent, suitable for chelating cationic transition metals in an oxidation alkali medium, in the composition having an alkaline pH. Concentrations, amounts, salts and molar ratios for the chelating agent in this composition, which have been disclosed hereinabove in detail, also apply the chelating agent in the ready-to-use hair dyeing and/or bleaching composition. The total molar concentration of chelating agents in the ready-to-use hair dyeing and/or bleaching composition may be at least 4.6 mM.

The hair oxidative dyeing or bleaching agents in the ready-to-use composition may be the same hair oxidative dyeing or bleaching agents as in the hair dyeing and/or bleaching composition.

The present disclosure also relates to a kit for dyeing and/or bleaching hair comprising individually packaged a) a composition having an alkaline pH and comprising an effective amount of at least one chelating agent, suitable for chelating cationic transition metals in an oxidation alkali medium; b) a hair dyeing and/or bleaching composition comprising at least one hair oxidative dyeing or bleaching agent, and c) an oxidizing composition comprising at least one oxidant.

The present disclosure also relates to a kit for dyeing and/or bleaching hair comprising individually packaged a) a composition comprising a cosmetically effective amount of at least one chelating agent, suitable for chelating cationic transition metals in an oxidation alkali medium; at least one hair oxidative dyeing or bleaching agent; wherein the composition is a hair dyeing and/or bleaching composition having an alkaline pH; and b) an oxidizing composition comprising at least one oxidant.

The oxidant may be hydrogen peroxide.

The chelating agent, suitable for chelating cationic transition metals in an oxidation alkali medium, in the kit is defined equally as the chelating agent, suitable for chelating cationic transition metals in an oxidation alkali medium, in the composition having an alkaline pH. Concentrations, amounts, salts and molar ratios for the chelating agent in this composition, which have been disclosed hereinabove in detail, also apply the chelating agent in the kit.

The hair oxidative dyeing or bleaching agents in the kit may be the same hair oxidative dyeing or bleaching agents as in the hair dyeing and/or bleaching composition.

The kit may also comprise at least one additional individually packaged composition for the hair care. The hair care composition may be a shampoo, an oil, a serum, a rinse-off hair conditioner, a rinse-off hair mask, a leave-on hair conditioner, a leave-on mask or a spray. The hair care composition may be a shampoo, a rinse-off hair conditioner or a rinse-off hair mask. The hair care product may also have an alkaline pH and comprise an effective amount of at least one chelating agent, suitable for chelating cationic transition metals in an oxidation alkali medium.

The term "hair care" refers to the maintenance of the qualities of the hair and includes the hair hygiene. These qualities are subject to improvement and maintained through a cosmetic treatment and/or care of the hair both in healthy subjects as well as those which present diseases and/or disorders of the scalp, such as and not restricted to, ulcers and lesions on the scalp, psoriasis, dermatitis, dandruff, or hair loss, among others.

The present disclosure also relates to the use of a composition having an alkaline pH and comprising an effective amount of at least one chelating agent, suitable for chelating cationic transition metals in an oxidation alkali medium; for decreasing and/or preventing color deviation in the hair, and/or chromaticity deviation, and/or hair damage provoked by a ready-to-use hair dyeing, and/or bleaching composition comprising at least one oxidant.

The oxidant may be hydrogen peroxide.

The chelating agent, suitable for chelating cationic transition metals in an oxidation alkali medium, in the use of a composition containing it, is defined equally as the chelating agent, suitable for chelating cationic transition metals in an oxidation alkali medium, in the composition having an alkaline pH. Concentrations, amounts, salts and molar ratios for the chelating agent in this composition, which have been disclosed hereinabove in detail, also apply the chelating agent in the use of a composition containing it. The total molar concentration of chelating agents in the ready-to-use hair dyeing and/or bleaching composition may be at least 4.6 mM.

The present disclosure also relates to a method for decreasing and/or preventing color deviation in the hair, and/or chromaticity deviation, and/or hair damage provoked by a ready-to-use hair dyeing, and/or bleaching composition comprising at least one oxidant, wherein a composition having an alkaline pH and comprising an effective amount of at least one chelating agent, suitable for chelating cationic transition metals in an oxidation alkali medium, is applied to the hair.

The present disclosure also relates to a method for dyeing and/or bleaching hair, which comprises applying to the hair a composition comprising a cosmetically effective amount of at least one chelating agent dissolved in a water-based medium, suitable for chelating cationic transition metals in an oxidation alkali medium; at least one hair oxidative dyeing or bleaching agent; at least one oxidant, and wherein the composition is a ready-to-use hair dyeing and/or bleaching composition having an alkaline pH, and rinsing the hair with water after an application time of the ready-to-use hair dyeing and/or bleaching composition in the hair from 1 minute to 1 hour.

The present disclosure also relates to a method for dyeing and/or bleaching hair, which comprises a) applying to the hair a composition having an alkaline pH and comprising an effective amount of at least one chelating agent, suitable for chelating cationic transition metals in an oxidation alkali medium, b) optionally rinsing the hair, c) optionally drying the hair, and d) applying a ready-to-use hair dyeing and/or bleaching composition comprising at least one hair oxidative dyeing or bleaching agent, and at least one oxidant, and rinsing the hair with water after an application time of the ready-to-use hair dyeing and/or bleaching composition in the hair from 1 minute to 1 hour.

The application time in the disclosed methods may last from 2 minutes to 50 minutes, from 5 minutes to 45 minutes, from 10 minutes to 40 minutes.

The oxidant may be hydrogen peroxide.

The chelating agent, suitable for chelating cationic transition metals in an oxidation alkali medium, in these methods is defined equally as the chelating agent, suitable for chelating cationic transition metals in an oxidation alkali medium, in the composition having an alkaline pH. Concentrations, amounts, salts and molar ratios for the chelating agent in this composition, which have been disclosed hereinabove in detail, also apply the chelating agent in these methods. The total molar concentration of chelating agents in the ready-to-use hair dyeing and/or bleaching composition may be at least 4.6 mM.

The hair oxidative dyeing or bleaching agents in these methods may be the same hair oxidative dyeing or bleaching agents as in the hair dyeing and/or bleaching composition.

The present disclosure also relates to a method for hair cosmetic treatment, which comprises a method for dyeing and/or bleaching hair, which comprises applying to the hair a composition comprising a cosmetically effective amount of at least one chelating agent dissolved in water, suitable for chelating cationic transition metals in an oxidation alkali medium; at least one hair oxidative dyeing or bleaching agent; at least one oxidant, and wherein the composition is a ready-to-use hair dyeing and/or bleaching composition having an alkaline pH, or a method for dyeing and/or bleaching hair, which comprises a) applying to the hair a composition having an alkaline pH and comprising an effective amount of at least one chelating agent, suitable for chelating cationic transition metals in an oxidation alkali medium, b) optionally rinsing the hair, c) optionally drying the hair, and d) applying a ready-to-use hair dyeing and/or bleaching composition comprising at least one hair oxidative dyeing or bleaching agent, and at least one oxidant, and rinsing the hair with water after an application time of the ready-to-use hair dyeing and/or bleaching composition in the hair from 1 minute to 1 hour, and at least one treatment step with at least one hair care product selected from the group of shampoos, conditioners, masks, sprays, oils and/or serums.

The application time in the disclosed methods may last from 2 minutes to 50 minutes, from 5 minutes to 45 minutes, from 10 minutes to 40 minutes.

The hair care product may be a shampoo, an oil, a serum, a rinse-off hair conditioner, a rinse-off hair mask, a leave-on hair conditioner, a leave-on mask, or a spray. The hair care composition may be a shampoo, a rinse-off hair conditioner, a rinse-off hair mask or a spray. The hair care product may also have an alkaline pH and comprise an effective amount of at least one chelating agent, suitable for chelating cationic transition metals in an oxidation alkali medium.

The treatment step with at least one hair care product may be before or after the treatment with the ready-to-use hair dyeing and/or bleaching composition, i.e., it may be a pre-treatment or a post-treatment.

The oxidant may be hydrogen peroxide.

The chelating agent, suitable for chelating cationic transition metals in an oxidation alkali medium, in this method is defined equally as the chelating agent, suitable for chelating cationic transition metals in an oxidation alkali medium, in the composition having an alkaline pH. Concentrations, amounts, salts and molar ratios for the chelating agent in this composition, which have been disclosed hereinabove in detail, also apply the chelating agent in this method. The total molar concentration of chelating agents in the ready-to-use hair dyeing and/or bleaching composition may be at least 4.6 mM.

The hair oxidative dyeing or bleaching agents in this method may be the same hair oxidative dyeing or bleaching agents as in the hair dyeing and/or bleaching composition.

The hair care product may comprise at least one additional cosmetic ingredient selected from the group of humectants, emollients, emulsifiers, surfactants, viscosity increasing ingredients, thickeners, binders, bulking agents, solvents, emulsion stabilizers, hair conditioners, natural extracts, antioxidants, pH adjusters, hair fixatives, film formers, UV filters, opacifying agents, fragrance ingredients, preservatives and cosmetic colorants.

Except in the Examples, or where otherwise explicitly indicated, all numerical quantities in this description specifying amounts of materials, application conditions, and the like, are to be understood as approximated, i.e., subject to a variability of plus or minus 5 percent, more preferably of plus or minus 3 percent, more preferably of plus or minus 1 percent, more preferably of plus or minus 0.1 percent, even more preferably of plus or minus 0.01 percent over the indicated value. It is to be understood that the upper and lower amount, range, and ratio limits set forth herein may be independently combined. Similarly, the ranges and amounts for each element of the technology described herein can be used together with ranges or amounts for any of the other elements.

EXAMPLES

The following examples are included for illustrative purposes only and should not be construed as limitations on the invention claimed herein.

Example 1

Booster composition 1

TABLE 1

| INGREDIENT (INCI Name) | % by weight |
|---|---|
| Aqua (Water (Eau)) | q.s.p. 100 |
| Tetrasodium Etidronate | 1.63 |
| Pentasodium Pentetate | 1.25 |

Example 2

Booster composition 2

TABLE 2

| INGREDIENT (INCI Name) | % by weight |
|---|---|
| Aqua (Water (Eau)) and other ingredients | q.s.p. 100 |
| Tetrasodium Etidronate | 6.43 |
| Pentasodium Pentetate | 5.15 |

Other ingredients: Cystine Bis-PG-Propyl Silanetriol, Sodium Sulfite, Arginine, Acrylates/Steareth-20 Itaconate Copolymer.

Example 3

Booster composition 3

TABLE 3

| INGREDIENT (INCI Name) | % by weight |
|---|---|
| Aqua (Water (Eau)) and other ingredients | q.s.p. 100 |
| Tetrasodium Etidronate | 5 |
| Pentasodium Pentetate | 4 |

Other ingredients: Cystine Bis-PG-Propyl Silanetriol, Sodium Sulfite.

Example 4

Color deviation and chromaticity deviation for a ready-to-use hair dyeing composition containing Booster composition 1 versus its comparative ready-to-use hair dyeing composition A ready-to-use hair dyeing composition is prepared by mixing 5 g of the Booster composition of example 1, with 150 g of a mixture 40:60 by weight of hair dye:developer, wherein the hair dye is the commercial product Revlonissimo Colorsmetique 7.44, by Revlon Professional, and the developer is the commercial product Creme Peroxide 20 vol. (6% by weight of hydrogen peroxide), by Revlon Professional.

Revlonissimo Colorsmetique 7.44 INCI ingredient list: Aqua/Water/Eau, Laureth-2, Isostearic Acid, Propylene Glycol, Glyceryl Stearate SE, Ethanolamine, Cetearyl Alcohol, Ammonium Hydroxide, Cocamidopropyl Betaine, Ammonium Lauryl Sulfate, Dimethicone, Ceteareth-20, Steartrimonium Chloride, Aminopropyl Phenyl Trimethicone, Erythorbic Acid, Glycerin, Hydrolyzed Hyaluronic Acid, Hydrolyzed Soy Protein, Isopropyl Alcohol, Polyquaternium-22, Polyquaternium-6, *Saccharomyces* Ferment Filtrate, Sodium Chloride, Tetrasodium EDTA, Parfum (Fragrance), Sodium Sulfite, 2-Methylresorcinol, 4-Amino-2-Hydroxytoluene, p-Aminophenol, p-Phenylenediamine, Titanium Dioxide.

Creme Peroxide 20 vol. INCI ingredient list: Aqua (Water) (Eau), Hydrogen Peroxide, Cetearyl Alcohol, Ceteareth-60, Cetyl Alcohol, Ceteareth-23, Phosphoric Acid, Pentasodium Pentetate, Sodium Stannate, Acrylates/Steareth-20 Itaconate Copolymer, Methylparaben.

The comparative ready-to-use composition is the previous mixture, without the booster of example 1, i.e. a mixture 40:60 by weight of hair dye:developer, wherein the hair dye is the commercial product Revlonissimo Colorsmetique 7.44, by Revlon Professional, and the developer is the commercial product Creme Peroxide 20 vol., by Revlon Professional.

The comparative ready-to-use composition was applied following the commercial instructions in hair locks without pollutant cationic metals, and in hair locks containing pollutant cationic metals. Hair locks containing pollutant cationic metals are prepared by immersing the hair in a water solution adjusted at pH 2.0-2.5 containing 2.5 ppm of $Fe^{2+}$ coming from $FeSO_4 \cdot 5H_2O$ and 7.5 ppm of $Cu^{2+}$ coming from $CuSO4 \cdot 7H_2O$, for 30 minutes, then, rinsing the hair with deionized water for 1 minute and blowing dry for 5 minutes. The composition containing the booster was applied also following the instructions for the comparative example in hair locks containing pollutant cationic metals. Table 4 shows the color deviation and chromaticity deviation for the comparative ready-to-use composition applied in hair locks containing pollutant cationic metals versus hair locks without pollutant cationic metals, and the ready-to-use composition containing the booster of example 1 applied in hair locks containing pollutant cationic metals versus the comparative ready-to-use composition applied in hair locks without pollutant cationic metals. Colorimetric measurements are performed on the hair locks using a spectrophotometer Konica Minolta CM-2600d, set up measurement conditions: UV 100%, illuminant D65, observer 2°, illumination area MAV (11 mm), specular component included, repeatability 3 times at 1.5 seconds interval.

TABLE 4

| | Color Deviation | Chromaticity Deviation |
|---|---|---|
| Ready-to-use composition containing Booster composition Example 1 vs Comparative composition in unpolluted hair | 3.54 | 3.18 |
| Comparative composition in polluted hair vs unpolluted hair | 6.67 | 6.09 |

Example 5

Color deviation and chromaticity deviation for a ready-to-use hair dyeing composition containing Booster composition 2 versus its comparative ready-to-use hair dyeing composition A ready-to-use hair dyeing composition is prepared by mixing 5 g of the Booster composition of example 2, with 150 g of a mixture 1:2 by weight of hair dye:developer, wherein the hair dye is the commercial product Young Color Excel 6.65, by Revlon Professional, and the developer is the commercial product Young Color Excel Plus Energizer 15 vol., by Revlon Professional.

Young Color Excel 6.65 INCI ingredient list: Aqua/Water/ Eau, Ethanolamine, Propylene Glycol, Laureth-2, Isostearic Acid, Glyceryl Stearate SE, 4-Amino-2-Hydroxytoluene, Stearyl Alcohol, Ammonium Lauryl Sulfate, Cocamidopropyl Betaine, Erythorbic Acid, Glycerin, Hydrolyzed Collagen, Hydrolyzed Wheat Protein, Isopropyl Alcohol, Polyquaternium-10, Polyquaternium-22, Polyquaternium-28, Sodium Acetate, Sodium Chloride, Tetrasodium EDTA, Parfum (Fragrance), Alpha-Isomethyl Ionone, Citronellol, Geraniol, Hexyl Cinnamal, Limonene, Linalool, Phenoxyethanol, Sodium Sulfite, Steartrimonium Chloride, 2-Methylresorcinol, Phenyl Methyl Pyrazolone, p-Aminophenol, p-Phenylenediamine.

Young Color Excel Plus Energizer 15 vol. INCI ingredient list: Aqua (Water) (Eau), Hydrogen Peroxide, Cetearyl Alcohol, Ceteareth-60, Cetyl Alcohol, Ceteareth-23, Phosphoric Acid, Pentasodium Pentetate, Sodium Stannate, Methylparaben.

The comparative ready-to-use composition is the previous mixture, without the booster of example 2, i.e. a mixture 1:2 by weight of hair dye:developer, wherein the hair dye is the commercial product Young Color Excel 6.65, by Revlon Professional, and the developer is the commercial product Young Color Excel Plus Energizer 15 vol. (4.5% by weight of hydrogen peroxide), by Revlon Professional.

The comparative ready-to-use composition was applied following the commercial instructions in hair locks without pollutant cationic metals, and in hair locks containing pollutant cationic metals. Hair locks containing pollutant cationic metals are prepared as described in example 4. The composition containing the booster was applied also following the instructions for the comparative example in hair locks containing pollutant cationic metals. Table 5 shows the color deviation and chromaticity deviation for the comparative ready-to-use composition applied in hair locks containing pollutant cationic metals versus hair locks without pollutant cationic metals, and the ready-to-use composition containing the booster of example 2 applied in hair locks containing pollutant cationic metals versus the comparative ready-to-use composition applied in hair locks without pollutant cationic metals. Colorimetric measurements are performed on the hair locks using a spectrophotometer Konica Minolta CM-2600d, set up measurement conditions: UV 100%, illuminant D65, observer 2°, illumination area MAV (11 mm), specular component included, repeatability 3 times at 1.5 seconds interval.

TABLE 5

|  | Color Deviation | Chromaticity Deviation |
| --- | --- | --- |
| Ready-to-use composition containing Booster composition Example 2 vs Comparative composition in unpolluted hair | 1.93 | 0.4 |
| Comparative composition in polluted hair vs unpolluted hair | 16.46 | 12.82 |

Table 5 shows that the color deviation and chromaticity deviation in hair locks are higher than 2, i.e, JND, for the comparative composition without the booster composition of example 2, and lower than 2, i.e not JND, in hair locks for the ready-to-use composition containing the booster composition of example 2.

Example 6

Color deviation and chromaticity deviation for a ready-to-use hair dyeing composition containing Booster composition 3 versus its comparative ready-to-use hair dyeing composition A ready-to-use hair dyeing composition is prepared by mixing 5 g of the Booster composition of example 3, with 150 g of a mixture 1:1 by weight of hair dye:developer, wherein the hair dye is the commercial product Revlonissimo Color Sublime 6.65, by Revlon Professional, and the developer is the commercial product Revlonissimo Color Sublime Technics 25 vol. (7.5% by weight of hydrogen peroxide), by Revlon Professional.

Revlonissimo Color Sublime 6.65 INCI ingredient list: Aqua/Water/Eau, Ethanolamine, Isostearic Acid, Glyceryl Stearate SE, Propylene Glycol, Laureth-4, 1-Hydroxyethyl 4,5-Diamino Pyrazole Sulfate, Stearyl Alcohol, Ammonium Lauryl Sulfate, 2-Methyl-5-Hydroxyethylaminophenol, Quaternium-91, Acrylates/Steareth-20 Itaconate Copolymer, Butylene Glycol, Cetearyl Alcohol, Cetrimonium Methosulfate, Erythorbic Acid, Mel/Honey/Miel, Polyquaternium-6, Rosa Moschata Seed Oil, Tetrasodium EDTA, Parfum (Fragrance), Sodium Sulfite, 4-Amino-2-Hydroxytoluene, Toluene-2,5-Diamine Sulfate, m-Aminophenol.

Revlonissimo Color Sublime Technics 25 vol. INCI ingredient list: Aqua (Water (Eau)), Paraffinum Liquidum (Mineral Oil (Huile Minérale)), Hydrogen Peroxide, Stearyl Alcohol, Ceteareth-20, Cetyl Alcohol, PEG-75 Lanolin, Phosphoric Acid, Etidronic Acid, Sodium Stannate, Sodium Benzoate.

The comparative ready-to-use composition is the previous mixture, without the booster of example 3, i.e. a mixture 1:1 by weight of hair dye:developer, wherein the hair dye is the commercial product Revlonissimo Color Sublime 6.65, by Revlon Professional, and the developer is the commercial product Revlonissimo Color Sublime Technics 25 vol., by Revlon Professional.

The comparative ready-to-use composition was applied following the commercial instructions in hair locks without pollutant cationic metals, and in hair locks containing pollutant cationic metals. Hair locks containing pollutant cationic metals are prepared as described in example 4. The composition containing the booster was applied also following the instructions for the comparative example in hair locks containing pollutant cationic metals. Table 6 shows the color deviation and chromaticity deviation for the comparative ready-to-use composition applied in hair locks containing pollutant cationic metals versus hair locks without pollutant cationic metals, and the ready-to-use composition containing the booster of example 3 applied in hair locks containing pollutant cationic metals versus the comparative ready-to-use composition applied in hair locks without pollutant cationic metals. Colorimetric measurements are performed on the hair locks using a spectrophotometer Konica Minolta CM-2600d, set up measurement conditions: UV 100%, illuminant D65, observer 2°, illumination area MAV (11 mm), specular component included, repeatability 3 times at 1.5 seconds interval.

TABLE 6

|  | Color Deviation | Chromaticity Deviation |
| --- | --- | --- |
| Ready-to-use composition containing Booster composition Example 3 vs Comparative composition in unpolluted hair | 1.47 | 1.27 |
| Comparative composition in polluted hair vs unpolluted hair | 11.32 | 10.33 |

Table 6 shows that the color deviation and chromaticity deviation in hair locks are higher than 2, i.e, JND, for the comparative composition without the booster composition of example 3, and lower than 2, i.e not JND, in hair locks for the ready-to-use composition containing the booster composition of example 3.

Example 7

Ready-to-use hair dyeing compositions containing Booster composition 3

Ready-to-use hair dyeing compositions are prepared by mixing 5 g of the Booster composition of example 3, with 150 g of different mixtures of hair dye and developer, shown in table 7.

TABLE 7

| Hair dye | Developer | Ratio hair dye:developer by weight |
|---|---|---|
| Wella Koleston 6/0 | Wella Koleston Developer 20 vol. | 1:1 |
| Wella Koleston 5/5 | Wella Koleston Developer 20 vol. | 1:1 |
| L'Oréal Majirel 6.0 | L'Oréal Developer 20 vol. | 40:60 |
| L'Oréal Majirel 5.5 | L'Oréal Developer 20 vol. | 40:60 |
| Revlonissimo Colorsmetique 5.5 | Creme Peroxide Developer 20 vol. | 40:60 |
| Revlonissimo Colorsmetique 6 | Creme Peroxide Developer 20 vol. | 40:60 |

Example 8

Effect of molar ratio of chelating agents in color deviation at constant total molar concentration of chelating agents.

A ready-to-use hair dyeing composition is prepared by mixing 6 g of antipollution booster composition containing water, tetrasodium etidronate and pentasodium pentetate, with 150 g of a mixture by weight 40:60 of hair dye:developer, wherein the hair dye is the commercial product Revlonissimo Colorsmetique 6.65, by Revlon Professional, and the developer is the commercial product Creme Peroxide 20 vol., by Revlon Professional.

Revlonissimo Colorsmetique 6.65 INCI ingredient list: Aqua/Water/Eau, Laureth-2, Isostearic Acid, Propylene Glycol, Glyceryl Stearate SE, Ethanolamine, Cetearyl Alcohol, Ammonium Hydroxide, Ammonium Lauryl Sulfate, Cocamidopropyl Betaine, 4-Amino-2-Hydroxytoluene, Aminopropyl Phenyl Trimethicone, Steartrimonium Chloride, Ceteareth-20, Dimethicone, Erythorbic Acid, Glycerin, Hydrolyzed Hyaluronic Acid, Hydrolyzed Soy Protein, Isopropyl Alcohol, Polyquaternium-22, Polyquaternium-6, Saccharomyces Ferment Filtrate, Sodium Chloride, Tetrasodium EDTA, Parfum (Fragrance), Sodium Sulfite, 2-Methylresorcinol, Phenyl Methyl Pyrazolone, p-Aminophenol, p-Phenylenediamine, Titanium Dioxide.

Each ready-to-use composition is applied once in one swatch containing pollutant cationic metals from each hair batch for 30 minutes. Each ready-to-use composition is applied on dry hair containing pollutant cationic metals at an amount by weight of 1:5 (swatch:ready-to-use composition). Hair swatches containing pollutant cationic metals are prepared as described in example 4. After 30 minutes, swatches are rinsed off thoroughly using tap water for 1 minute, until all ready-to-use composition is removed.

Then, each swatch is washed in 250 ml of solution of 10% Post Color Shampoo, for 30 seconds and 1000 rpm. Finally, swatches are rinsed off thoroughly using tap water for 1 minute, until all shampoo is eliminated and blown dry for 5 minutes.

The comparative ready-to-use composition is a mixture by weight 40:60 of hair dye:developer, wherein the hair dye is the commercial product Revlonissimo Colorsmetique 6.65, by Revlon Professional, and the developer is the commercial product Creme Peroxide 20 vol., by Revlon Professional. The comparative ready-to-use composition is applied following the protocol described in this example but in swatches without pollutant cationic metals or, as comparative example, in swatches containing pollutant cationic metals.

Table 8 shows the color deviation ($\Delta E$) for the comparative ready-to-use composition applied in swatches containing pollutant cationic metals versus swatches without pollutant cationic metals, and the ready-to-use compositions containing the antipollution booster compositions with different molar ratios tetrasodium etidronate:pentasodium pentetate at constant total molar concentration of chelating agents (8 mM of chelating agents in the ready-to-use compositions), versus the comparative ready-to-use composition applied in swatches without pollutant cationic metals.

TABLE 8

| | Molar ratio Tetrasodium Etidronate:Pentasodium Pentetate | Color Deviation |
|---|---|---|
| Comparative ready-to-use composition in polluted swatches vs unpolluted swatches | No booster | 4.85 |
| Ready-to-use composition containing booster ratio 1 vs Comparative ready to use composition in unpolluted swatches | 15:1 | 2.26 |
| Ready-to-use composition containing booster ratio 2 vs Comparative ready to use composition in unpolluted swatches | 8:1 | 2.52 |
| Ready-to-use composition containing booster ratio 3 vs Comparative ready to use composition in unpolluted swatches | 3:1 | 1.49 |
| Ready-to-use composition containing booster ratio 4 vs Comparative ready to use composition in unpolluted swatches | 2:1 | 0.52 |
| Ready-to-use composition containing booster ratio 5 vs Comparative ready to use composition in unpolluted swatches | 1.55:1 | 1.49 |
| Ready-to-use composition containing booster ratio 6 vs Comparative ready to use composition in unpolluted swatches | 1.25:1 | 1.55 |
| Ready-to-use composition containing booster ratio 7 vs Comparative ready to use composition in unpolluted swatches | 1:5 | 2.50 |

Example 9

Effect of molar concentration of chelating agents in color deviation at constant molar ratio of chelating agents A ready-to-use hair dyeing composition is prepared by mixing 6 g of antipollution booster composition containing water, tetrasodium etidronate and pentasodium pentetate at molar ratio 2:1 Tetrasodium Etidronate:Pentasodium Pentetate, with 150 g of a mixture by weight 40:60 of hair dye:developer, wherein the hair dye is the commercial product Revlonissimo Colorsmetique 6.65, by Revlon Professional, and the developer is the commercial product Creme Peroxide 20 vol., by Revlon Professional.

Each ready-to-use composition is applied following the protocol disclosed in example 8.

The comparative ready-to-use composition is the same one than in example 8 and it is applied following the same protocol than in example 8.

Table 9 shows the color deviation (ΔE) for the comparative ready-to-use composition applied in swatches containing pollutant cationic metals versus swatches without pollutant cationic metals, and the ready-to-use compositions containing the antipollution booster compositions with different molar concentrations of chelating agents at constant total molar ratio tetrasodium etidronate:pentasodium pentetate 2:1, versus the comparative ready-to-use composition applied in swatches without pollutant cationic metals.

TABLE 9

| | Total molar concentration of Tetrasodium Etidronate and Pentasodium Pentetate in the ready-to-use composition | Total amount of chelating agents in the booster by weight | Color Deviation |
|---|---|---|---|
| Comparative ready-to-use composition in polluted swatches vs unpolluted swatches | No booster | No booster | 5.61 |
| Ready-to-use composition containing booster at molar concentration 1 vs Comparative ready-to-use composition in unpolluted swatches | 1 mM | 0.95% | 4.04 |
| Ready-to-use composition containing booster at molar concentration 2 vs Comparative ready-to-use composition in unpolluted swatches | 2.5 mM | 2.37% | 2.81 |
| Ready-to-use composition containing booster at molar concentration 3 vs Comparative ready-to-use composition in unpolluted swatches | 4.6 mM | 4.36% | 2.00 |
| Ready-to-use composition containing booster at molar concentration 4 vs Comparative ready-to-use composition in unpolluted swatches | 6 mM | 5.69% | 1.76 |
| Ready-to-use composition containing booster at molar concentration 5 vs Comparative ready-to-use composition in unpolluted swatches | 7.5 mM | 7.12% | 0.86 |
| Ready-to-use composition containing booster at molar concentration 6 vs Comparative ready-to-use composition in unpolluted swatches | 18 mM | 17.08% | 1.09 |

Table 9 shows that the color deviation in dyed hair swatches is 2 or lower than 2, i.e. not JND, when the total molar concentration of chelating agents at the ready-to-use composition is at least 4.6 mM, or the total amount of chelating agents in the booster is at least 4.36%.

The invention claimed is:

1. A composition having an alkaline pH and comprising an effective amount of at least one chelating agent, suitable for chelating cationic transition metals in an oxidation alkali medium,
    wherein the effective amount of the at least one chelating agent ranges from 4.36% to 17.08% by weight based on the total weight of the composition, and
    wherein the at least one chelating agent is a mixture of at least one salt of etidronic acid and at least one salt of diethylenetriamine pentaacetic acid, the molar ratio of the at least one salt of etidronic acid to the at least one salt of diethylenetriamine pentaacetic acid ranging from 3:1 to 1.2:1.

2. The composition according to claim 1, wherein the composition comprises at least one hair strengthener, and/or at least one free radical scavenger.

3. The composition according to claim 1, wherein the composition is a cosmetic composition.

4. The composition according to claim 1, wherein the composition is a hair cosmetic composition.

5. A composition, the composition comprising:
    a cosmetically effective amount of at least one chelating agent dissolved in a water-based medium, suitable for chelating cationic transition metals in an oxidation alkali medium;
    at least one hair oxidative dyeing or bleaching agent; and
    at least one oxidant,
    wherein the composition is a ready-to-use hair dyeing and/or bleaching composition having an alkaline pH,
    wherein the total molar concentration of the at least one chelating agent in the composition ranges from 4.6 mM to 18 mM, and
    wherein the chelating agent is a mixture of at least one salt of etidronic acid and at least one salt of diethylenetriamine pentaacetic acid, the molar ratio of the at least one salt of etidronic acid to the at least one salt of diethylenetriamine pentaacetic acid ranging from 3:1 to 1.2:1.

6. The composition according to claim 1, wherein the composition is a part of a kit for dyeing and/or bleaching hair, wherein the composition is individually packaged and the kit further comprises an individually packaged hair dyeing and/or bleaching composition comprising at least one hair oxidative dyeing or bleaching agent, and an individually packaged oxidizing composition comprising at least one oxidant.

7. The composition according to claim 1, wherein the composition is used for decreasing and/or preventing color deviation in the hair, and/or chromaticity deviation, and/or hair damage provoked by a ready-to-use hair dyeing, and/or bleaching composition comprising at least one oxidant.

8. The composition according to claim 5, wherein the composition is applied to the hair, and wherein the hair is rinsed with water after an application time of the ready-to-use hair dyeing and/or bleaching composition in the hair from 1 minute to 1 hour.

9. A method for dyeing and/or bleaching hair, the method comprising:
   a) applying to the hair a composition having an alkaline pH and comprising an effective amount of at least one chelating agent, suitable for chelating cationic transition metals in an oxidation alkali medium,
   wherein the effective amount of the at least one chelating agent ranges from 4.36% to 17.08% by weight based on the total weight of the composition, and
   wherein the chelating agent is a mixture of at least one salt of etidronic acid and at least one salt of diethylenetriamine pentaacetic acid, the molar ratio of the at least one salt of etidronic acid to the at least one salt of diethylenetriamine pentaacetic acid ranging from 3:1 to 1.2:1;
   b) optionally rinsing the hair;
   c) optionally drying the hair; and
   d) applying a ready-to-use hair dyeing and/or bleaching composition comprising at least one hair oxidative dyeing or bleaching agent, and at least one oxidant, and rinsing the hair with water after an application time of the ready-to-use hair dyeing and/or bleaching composition in the hair from 1 minute to 1 hour.

10. The method of claim 9, the method further comprising at least one treatment step with at least one hair care product selected from the group of shampoos, conditioners, masks, sprays, oils and/or serums.

11. The composition according to claim 8, and wherein the hair is treated with at least one treatment step with at least one hair care product selected from the group of shampoos, conditioners, masks, sprays, oils and/or serums.

12. A method for dyeing and/or bleaching hair, the method comprising:
   applying to the hair a composition comprising:
      a cosmetically effective amount of at least one chelating agent dissolved in a water-based medium, suitable for chelating cationic transition metals in an oxidation alkali medium; at least one hair oxidative dyeing or bleaching agent; and
      at least one oxidant,
      wherein the composition is a ready-to-use hair dyeing and/or bleaching composition having an alkaline pH;
      wherein the total molar concentration of the at least one chelating agent in the ready-to-use composition ranges from 4.6 mM to 18 mM; and
      wherein the chelating agent is a mixture of at least one salt of etidronic acid and at least one salt of diethylenetriamine pentaacetic acid, the molar ratio of the at least one salt of etidronic acid to the at least one salt of diethylenetriamine pentaacetic acid ranging from 3:1 to 1.2:1; and
   rinsing the hair with water after an application time of the ready-to-use hair dyeing and/or bleaching composition in the hair from 1 minute to 1 hour.

* * * * *